United States Patent
Hosokawa et al.

(10) Patent No.: US 8,317,847 B2
(45) Date of Patent: Nov. 27, 2012

(54) BIOSTIMULATION APPARATUS, GENE CONTROL APPARATUS, AND MUSCLE-RELATED DISORDER THERAPEUTIC APPARATUS

(75) Inventors: Yoichiro Hosokawa, Takarazuka (JP); Hiroshi Masuhara, Higashiosaka (JP); Kazunori Okano, Kobe (JP); Yutaka Takaoka, Kobe (JP); Mika Ohta, Kobe (JP); Akihiko Ito, Mitaka (JP)

(73) Assignees: Japan Science and Technology Agency, Kawaguchi-shi (JP); National University Corporation Kobe University, Kobe-shi (JP)

( * ) Notice: Subject to any disclaimer, the term of this patent is extended or adjusted under 35 U.S.C. 154(b) by 361 days.

(21) Appl. No.: 12/678,998

(22) PCT Filed: Sep. 18, 2008

(86) PCT No.: PCT/JP2008/002577
§ 371 (c)(1),
(2), (4) Date: Jun. 28, 2010

(87) PCT Pub. No.: WO2009/037841
PCT Pub. Date: Mar. 26, 2009

(65) Prior Publication Data
US 2010/0280580 A1 Nov. 4, 2010

(30) Foreign Application Priority Data
Sep. 19, 2007 (JP) ............................... 2007-242851

(51) Int. Cl.
*A61N 5/06* (2006.01)
*A61N 7/00* (2006.01)
*A61F 7/12* (2006.01)

(52) U.S. Cl. .............................. 607/89; 607/99; 607/108

(58) Field of Classification Search ............... 607/89, 607/99, 108
See application file for complete search history.

(56) References Cited

FOREIGN PATENT DOCUMENTS

| | | |
|---|---|---|
| JP | 62-14868 | 1/1987 |
| JP | 62-19183 A | 1/1987 |
| JP | 63-57062 | 11/1988 |
| JP | 01-151458 | 6/1989 |
| JP | 02-031768 | 2/1990 |
| JP | 03-292959 | 12/1991 |
| JP | 07-016304 | 1/1995 |
| JP | 08-229096 | 9/1996 |
| JP | 2004-298208 | 10/2004 |
| JP | 2005-205446 | 8/2005 |
| WO | WO-02/40974 | 5/2002 |
| WO | WO-2005/089039 | 9/2005 |
| WO | WO-2006/089227 | 8/2006 |

OTHER PUBLICATIONS

Niimi et al., "Asian traditional medicine: from molecular biology to organ circulation," Clinical Hemorheology and Microcirculation 23 (2000) pp. 123-123.
Thomas et al., "Myostatin, a Negative Regulator of Muscle Growth, Functions by Inhibiting Myoblast Proliferation," The Journal of Biological Chemistry, Dec. 22, 2000, pp. 40235-40243.
International Search Report for PCT/JP2008/002577, mailed Nov. 4, 2008.

*Primary Examiner* — Armando Rodriguez
(74) *Attorney, Agent, or Firm* — Marshall, Gerstein & Borun LLP

(57) ABSTRACT

A biostimulation apparatus of the present invention includes a laser oscillator for oscillating an ultra short pulsed laser beam and an optical system for focusing the ultra short pulsed laser beam, wherein the ultra short pulsed laser beam is focused by the optical system at a target portion of a living subject to cause the target portion to be irradiated with the laser beam to stimulate an acupuncture point, and wherein the target portion is either the acupuncture point or its periphery.

20 Claims, 6 Drawing Sheets

NORMAL MOUSE
SKELETAL MUSCLE

ONE-SECOND
IRRADIATION

FEMTOSECOND
ONE-SHOT
IRRADIATION (a)　　　　　　　　(b)　　　　　　　　(c)

BIOSTIMULATION APPARATUS, GENE CONTROL APPARATUS, AND MUSCLE-RELATED DISORDER THERAPEUTIC APPARATUS

TECHNICAL FIELD

This invention relates to a biostimulation apparatus that has a laser oscillator, to a gene control apparatus, and to a muscle related disorder therapeutic apparatus.

BACKGROUND ART

In recent years, attention has been paid to Eastern medicines. Especially, acupuncture-moxibustion, which is a medical treatment method having the longest history as a traditional medicine, attracts attention, and WHO (World Health Organization), too, recognizes the efficacy thereof. According to the accumulated knowledge from the traditional medicines or according to the scientific approaches based on the anatomy physiology, acupuncture treatment has been performed by sticking an extremely fine metal needle into the body of a subject at an acupuncture point (meridian point). Acupuncture treatment has been used for the healing of a variety of disorders as well as for anaesthesia. Moreover, acupuncture treatment has been used in a wide range of fields with a view to preventing and treating the stiffness and pain in nape, shoulder, lower back, and joints and the pain after sports activities.

Acupuncture-like therapeutic treatments, such as percutaneous low-frequency electric stimulation, laser acupuncture and other like therapy, have been provided as a substitute for the acupuncture treatment employing metal needles that have been used traditionally in the past. Such therapeutic techniques involve no direct insertion of acupuncture needles. Therefore, no damage will be caused to tissues of the skin, nerve, blood vessel and the like, and therapeutic treatment can usually be performed using painless stimulation. For the case of the percutaneous low-frequency electric stimulation, spiny triangular cone-like electrodes for energization are placed on acupuncture points and fixed there with adhesive plaster or other like material, and low-frequency energization is conducted. In addition, the laser acupuncture is described, for example, in the following Patent Document 1. This Patent Document 1 describes a laser unit for acupuncture treatment, and it is set forth therein that acupuncture treatment is performed by the irradiation of a therapeutic target point with a low-level laser beam (average output up, at most, to 3 mW) oscillated from a semiconductor laser.

Patent Document 1: JP-A-08-229096

DISCLOSURE OF INVENTION

Technical Problem

According to the laser unit as set forth in Patent Document 1, by the irradiation of a therapeutic target point with a low-level laser beam, thermal stimulation is applied to an irradiated portion. That is, it is conceivable that this laser unit intends to achieve the same therapeutic effects as the moxibustion. When compared to any other techniques, therapeutic treatment may be performed in an extremely easy manner. In addition, the controlling of an irradiation position or the like, too, is thought to be easy, but nonetheless it is difficult to obtain, by thermal stimulation alone, the same effects as the general acupuncture treatment. Besides, there is a risk of causing excessive thermal damage to the irradiated tissue.

An object of the present invention is to provide a biostimulation apparatus capable of acupuncture-like stimulation without the insertion of an acupuncture needle into the body of a living subject.

Means for Solving Problem

The inventors of the present application advanced the research on nonlinear phenomena induced by a high-intense femtosecond laser beam to a variety of irradiation targets. These inventors succeeded in applying, by the focused irradiation of a living subject with a femtosecond laser beam, stimulation useful for the living subject without necrotizing cells around the beam focal spot. Based on these pieces of knowledge, the present invention was made.

More specifically, the present invention provides a biostimulation apparatus which includes a laser oscillator for oscillating an ultra short pulsed laser beam and an optical system for focusing the ultra short pulsed laser beam, wherein the ultra short pulsed laser beam is focused by the optical system at a target portion of a living subject to cause the target portion to be irradiated with the laser beam to stimulate an acupuncture point, and wherein the target portion is either the acupuncture point or its periphery. The acupuncture point is stimulated, for example, by physical impact caused by the irradiation with the ultra short pulsed laser beam. In the biostimulation apparatus, it is preferred that irradiation with the ultra short pulsed laser beam is so conducted as not to discontinue the continuity of a living tissue. The target portion can be so selected as to be situated, for example, either in a skin tissue or in a muscle tissue.

The biostimulation apparatus may be so configured as to further include an acupuncture point detection means for detecting an acupuncture point and a control means for deciding the target portion based on information from the acupuncture point detection means. The biostimulation apparatus can be used as an apparatus for enhancing improvement in blood flow.

In addition, the present invention provides a gene control apparatus which includes a laser oscillator for oscillating an ultra short pulsed laser beam and an optical system for focusing the ultra short pulsed laser beam, wherein the ultra short pulsed laser beam is focused by the optical system at a target portion of a living subject to cause the target portion to be irradiated with the laser beam to control an expression level of a particular gene. The expression level of the particular gene is controlled using, for example, physical impact caused by the irradiation with the ultra short pulsed laser beam. In the gene control apparatus, it is preferred that irradiation with the ultra short pulsed laser beam is so conducted as not to discontinue the continuity of a living tissue.

The gene control apparatus can be used as an apparatus that implements a method in which the ultra short pulsed laser beam is focused, by the optical system, at a target portion in a muscle tissue of the living subject to cause the target portion to be irradiated with the laser beam to control an expression level of a myostatin gene in the muscle tissue. The enhancement or the restoration of the muscle tissue or both can be accelerated by controlling the expression level of the myostatin gene.

In addition, the present invention provides a muscle related disorder therapeutic apparatus which includes a laser oscillator for oscillating an ultra short pulsed laser beam and an optical system for focusing the ultra short pulsed laser beam, wherein the ultra short pulsed laser beam is focused by the optical system at a target portion in a muscle tissue of a living subject to cause the target portion to be irradiated with the laser beam to treat a muscle related disorder. The muscle related disorder is treated using, for example, physical impact caused by the irradiation with the ultra short pulsed laser beam. In the muscle related disorder therapeutic apparatus, it is preferred that irradiation with the ultra short pulsed laser beam is so conducted as not to discontinue the continuity of a living tissue.

Advantageous Effects of Invention

The biostimulation apparatus, the gene control apparatus, and the muscle related disorder therapeutic apparatus of the present invention respectively make it possible to apply acupuncture-like stimulation to a living subject, to control a gene, and to treat a muscle related disorder, without contact to a living tissue and, in addition, without difficulty and complication.

Figure 1:
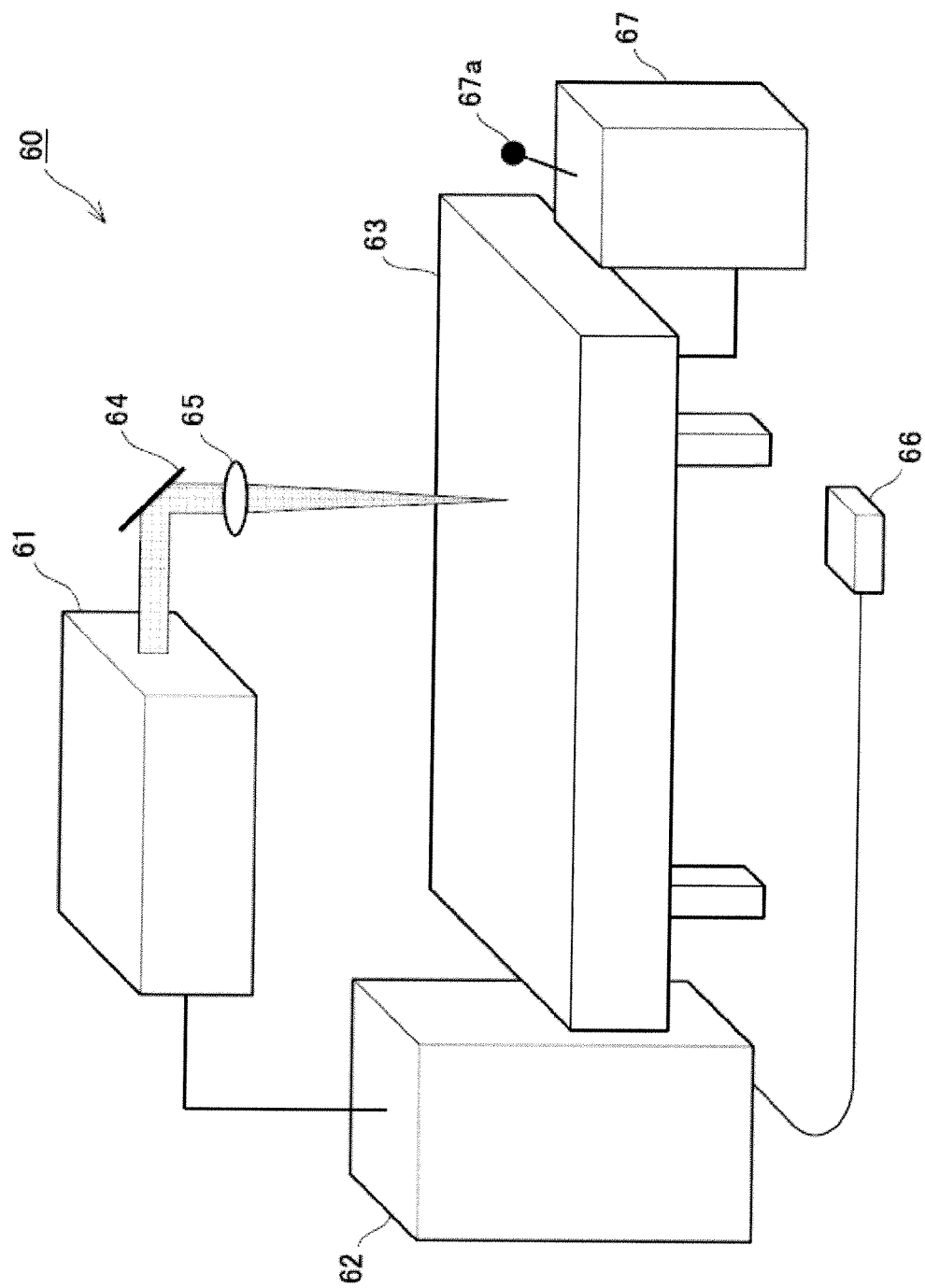
FIG. 1 is a schematic diagram showing a schematic configuration of a biostimulation apparatus according to a first embodiment of the present invention.

| REFERENCE SIGNS LIST | |
|---|---|
| 1 | main unit |
| 2 | electric power supply part |
| 3 | control part |
| 4 | laser part |
| 5 | electric power supply key switch |
| 6 | console panel |
| 7, 15 | laser guide |
| 9 | optical connector |
| 10 | foot switch |
| 12 | laser oscillator |
| 16 | pulse expander |
| 20 | irradiation gun |
| 21 | laser beam output end |
| 22 | objective lens |
| 23 | biostimulation apparatus |
| 24 | pulse compressor |
| 51 | laser oscillator |
| 52 | single lens |

| REFERENCE SIGNS LIST | |
|---|---|
| 53 | mechanical shutter |
| 54 | irradiation-guide laser oscillator |
| 55 | irradiation target |
| 60 | biostimulation apparatus |
| 61 | laser oscillator |
| 62 | control unit |
| 63 | treatment table |
| 64 | reflection board |
| 65 | beam focusing lens |
| 66 | foot pedal |
| 67 | treatment table control unit |
| 67a | control lever |

BEST MODE FOR CARRYING OUT INVENTION

Hereinafter, the present invention will be described in more detail. A biostimulation apparatus according to the present invention implements a biostimulation method. The biostimulation apparatus of the present invention includes a laser oscillator for irradiating a living subject with an ultra short pulsed laser beam. In addition thereto, the biostimulation apparatus is provided with an optical system for converging the ultra short pulsed laser beam from the laser oscillator at a target portion. The depth of irradiation can be adjusted by controlling the position of the optical system, whereby it becomes possible to irradiate a surface tissue of the living subject and a tissue under the surface of the living subject with the laser beam. The irradiation with the ultra short pulsed laser beam gives rise to physical impact, and a specific portion of the living subject (such as, for example, an acupuncture point) can be stimulated by such physical impact. By "physical impact" in the present specification caused by the irradiation with the ultra short pulsed laser beam is meant physical impact which is caused by the transmission of stress (generated by at least one of destruction, shockwave generation, cavitation bubble generation, air bubble generation, and convection flow generation induced at a portion to which the ultra short pulsed laser beam is focused and which is irradiated with the laser beam) around the aforesaid laser beam focused and irradiated portion.

The conventional laser acupuncture treatment without the use of the ultra short pulsed laser beam is to expect the efficacy of treatment by thermal stimulation or photochemical stimulation, and such stimulation is based on one-photon absorption in the tissue surface. However, for the case of the ultra short pulsed laser beam used in the present invention, it is possible to inject, by means of multi-photon absorption caused by photons concentrated in an extremely short duration, energy into the inside of a living subject in a wavelength region showing high permeability with respect to the tissue of the living subject. In addition, since such energy injection is accomplished in a much less time than the time required for thermogenesis (from $1.0 \times 10^{-9}$ to $1.0 \times 10^{-6}$ (sec)), this makes it possible to stimulate a target portion by physical impact almost with causing less thermal stimulation to the target portion. Therefore, in the present invention, the ultra short pulsed laser beam is focused not on the surface of the living subject but at a tissue under the surface of the living subject, thereby making it possible to expect, without causing any thermal damage to the tissue cells around the laser beam focal spot, the effect of biostimulation, the effect of gene control, the effect of muscle related disorder treatment, and other like effect.

It is preferred that the ultra short pulsed laser beam of the present invention is a picosecond pulsed laser beam or a femtosecond pulsed laser beam and the latter is more preferable. To sum up, the pulse duration of the ultra short pulsed laser beam is preferably in the range of from $1.0\times10^{-10}$ to $1.0\times10^{-15}$ (sec), and more preferably in the range of from $1.0\times10^{-12}$ to $1.0\times10^{-15}$ (sec). The transient light intensity of the ultra short pulsed laser beam is, for example, $5\times10^5$ (W) or higher, preferably $2\times10^9$ (W) or higher. The upper limit of the transient light intensity of the ultra short pulsed laser beam, although it is not specifically limited, is, for example, $1\times10^{18}$ (W) or less (preferably $1\times10^{15}$ (W) or less, and more preferably $1\times10^{12}$ (W) or less).

Since the product of the density (W) times the pulse duration (sec) of the ultra short pulsed laser beam is the light pulse energy (J/pulse), the condition of the laser beam can be set as in Table 1 depending upon the duration. In addition, in Table 1, the laser beam intensity A shows the case when the transient light intensity is not less than $5\times10^5$ (W) but below $2\times10^9$ (W) while the laser beam intensity B shows the case when the transient light intensity B is $2\times10^9$ (W) or higher.

TABLE 1

| | Pulse Duration (sec) | Laser Pulse Energy A (J/pulse) | Laser Pulse Energy B (J/pulse) |
|---|---|---|---|
| Picosecond Pulsed Laser Beam | | | |
| General Range | $1.0\times10^{-10}$~$1.0\times10^{-12}$ | $0.5\times10^{-3}$~$0.5\times10^{-6}$ | $2$~$2\times10^{-3}$ |
| Preferable Range | $1.0\times10^{-11}$~$1.0\times10^{-12}$ | $0.5\times10^{-3}$~$0.5\times10^{-6}$ | $2\times10^{-2}$~$2\times10^{-3}$ |
| Femtosecond Pulsed Laser Beam | | | |
| General Range | $1.0\times10^{-12}$~$1.0\times10^{-15}$ | $0.5\times10^{-6}$~$0.5\times10^{-9}$ | $2\times10^{-3}$~$2\times10^{-6}$ |
| Preferable Range | $1.0\times10^{-13}$~$1.0\times10^{-15}$ | $0.5\times10^{-7}$~$0.5\times10^{-9}$ | $2\times10^{-4}$~$2\times10^{-6}$ |

The wavelength of the ultra short laser beam is not specifically limited and may be selected from within the range between 200 nm and 2000 nm, preferably from within the range between 600 nm and 1200 nm. If the laser beam wavelength is set to fall within the range between 600 nm and 1200 nm, this setting is especially preferable because, for the case of irradiation at a desired depth from the skin surface, absorption by major tissues until the arrival at a target portion is low and therefore the target portion can be irradiated with laser beam while maintaining the intensity thereof. Irradiation with ultra short pulsed laser beam may be conducted in a one-shot manner or repeatedly in a multi-shot manner. For example, the number of shots may be set to fall within the range between one shot and 10,000,000 shots. In addition, although the repetition frequency of the ultra short pulsed laser beam in the case of repetitive irradiation in a multi-shot manner is not specifically limited, it may be set to fall, for example, within the range between 1 Hz and 100 MHz. It is preferable to set the pulse duration, the intensity, the wavelength, the number of times of irradiation, and the repetition frequency of the ultra short pulsed laser beam so that tissue necrosis is not caused while local mechanical destruction occurs at a laser-beam focused and irradiated portion. In addition, preferably, a fixed point is irradiated with the laser beam without being scanned. In addition, it is preferable that irradiation is conducted under the condition that will not discontinue the continuity of a tissue of the living subject that is a target for irradiation. In other words, irradiation is preferably carried out under conditions in which no incision of the skin tissue occurs.

The laser oscillator is not limited to the specific one and it is advisable to select a laser oscillator capable of oscillating a laser beam of desired pulse duration and intensity, such as, for example, picosecond/femtosecond titanium-sapphire laser, femtosecond fiber laser, picosecond $Nd^{3+}$:YAG laser, picosecond $Nd^{3+}$:VYO$_4$ laser, excimer laser and the like.

In the biostimulation apparatus of the present invention, ultra short pulsed laser beam is focused at a target portion of the body of a human or non-human animal for irradiation thereof to stimulate an acupuncture point. Such a target portion is either an acupuncture point or its periphery. The irradiation of a target portion with ultra short pulsed laser beam gives rise to impact waves at the target portion and the acupuncture point is stimulated by the transmission of such impact waves. In addition, it has been recognized that the improvement in blood flow can be accelerated by stimulating an acupuncture point (see Niimi H. Yuwono H S, Asian traditional medicine: from molecular biology to organ circulation. Clin Hemorheol Microcirc 23: 123-125, 2000). Therefore, the biostimulation apparatus of the present invention can be used as an apparatus for implementing a method for enhancing the improvement in blood flow. The acupuncture point, i.e., the target for stimulation by the biostimulation apparatus of the present invention, is not limited to the specific one but is intended for every acupuncture point. The acupuncture point includes, for example, an acupuncture point called "kensei" (abbreviated GB-21 which is an abbreviation of WHO International Standard revised in Acupuncture and Moxibustion Meridian Point Nomenclature Standardization International Conference held in Geneva, October, 1989. The same is applied to the following abbreviations), an acupuncture point called "tenchu" (abbreviated BL-10), and an acupuncture point called "tenosanri" (abbreviated LI-10) which are said to have efficacy for shoulder stiffness, and an acupuncture point called "taikei" (abbreviated KI-3), an acupuncture point called "saninko" (abbreviated SP-6), and an acupuncture point called "taisho" (abbreviated LR-3) which are said to have efficacy for leg coldness.

A gene expression control apparatus according to the present invention has the same configuration as the aforesaid biostimulation apparatus. For example, the gene expression control apparatus of the present invention can be used either as an apparatus for implementing a method of controlling the expression of a myostatin gene which is a gene for controlling the activity of a muscle tissue or as an apparatus for implementing a method for the reinforcement/enhancement of a muscle tissue such as the growth of a muscle tissue. In the gene expression control apparatus of the present invention, irradiation is preferably applied to a muscle tissue or its periphery in the case of controlling the expression of a myostatin gene. In addition, irradiation is preferably carried out under conditions that will not discontinue the continuity of a tissue of the living subject. In other words, irradiation is preferably carried out under conditions that will not cause, for example, skin tissue incision.

A muscle related disorder therapeutic apparatus according to the present invention has the same configuration as the aforesaid biostimulation apparatus. The muscle related disorder therapeutic apparatus can be used as an apparatus for implementing a method for preventing and treating a muscle related disorder by irradiating a muscle tissue or its periphery with the ultra short pulsed laser beam. The muscle related disorder includes, for example, shoulder stiffness, frozen shoulder (stiff shoulder due to age), rheumatoid arthritis, myofascitis, neck muscle rigidity, neck-shoulder-arm syndrome, whiplash syndrome, sprain, tendon sheath inflammation, low back pain syndrome, skeletal muscle atrophy and the like. In addition, irradiation is preferably carried out under conditions that will not discontinue the continuity of a tissue of the living subject. In other words, irradiation is preferably carried out under conditions that will not cause, for example, skin tissue incision.

In the biostimulation apparatus, the gene control apparatus, and the muscle related disorder therapeutic apparatus of the present invention, the depth of laser beam irradiation against the living subject is not limited when the ultra short pulsed laser beam is focused at a tissue under the surface of the living subject; however, it is preferred that irradiation is focused at a depth in a range of from 100 μm to 1 cm from the surface of the living subject is preferable, more preferably at depths in the range of from 1 mm to 5 mm.

Hereinafter, embodiments of the biostimulation apparatus according to the present invention will be described.

First Embodiment

FIG. 1 is a schematic diagram showing a schematic configuration of a biostimulation apparatus according to a first embodiment of the present invention. In a biostimulation apparatus 60, an ultra short pulsed laser beam oscillated from a laser oscillator 61 is focused and emitted, via a reflection board 64 and then via a beam focusing lens 65, over a treatment table 63. A control unit 62 is connected to the laser oscillator 61. The control unit 62 controls the irradiation condition of the laser oscillator 61, such as conditions for laser pulse repetition frequency, laser beam intensity, pulse duration, wavelength, pulse number, and focus depth (in the depth direction of a focal spot) in the laser beam irradiation target. The control unit 62 is provided with a console part (not shown), thereby enabling an operator to set irradiation conditions by manipulating the console part. The controlling of the aforesaid irradiation conditions by means of the control unit 62 may be either based on the information fed through the console part by the operator, or conducted automatically with the aid of a computer or other like means. In addition, a foot pedal 66 is connected to the control unit 62. The control unit 62 detects an operation of the foot pedal 66 and controls the on/off of the output of the laser oscillator 61. Connected to the treatment table 63 is a treatment table control unit 67. The treatment table control unit 67 is provided with a control lever 67a. In response to an operation of the control lever 67a, the treatment table control unit 67 three-dimensionally drives the treatment table 63 and controls the position of the treatment table 63 on a two-dimensional surface as well as in a vertical direction.

A description will now be given of how to use the above-described biostimulation apparatus 60. In the first place, an irradiation portion of the body of a subject is fixed onto the treatment table 63. The subject is either a human or a non-human animal. The position of the subject is not specifically limited. For example, the subject may lay down or seat on the treatment table 63. Alternatively, a part of the body of the subject including the irradiation portion may be placed on the treatment table 63. For example, the biostimulation apparatus 60 may be used in such a manner that an arm or arms of the subject are placed on the treatment table 63. The beam focal position (in lateral direction and in longitudinal direction) can be regulated by adjusting the placement position of the body of the subject on the treatment table 63. In addition, the operator is able to make an adjustment in the position of irradiation by regulating the position of the treatment table 63 with the aid of the control lever 67a. Next, the operator sets a condition for irradiation by the console part of the control unit 62. Then, the operator manipulates the foot pedal 66 for the target portion to be irradiated with the laser beam.

The biostimulation apparatus 60 of the first embodiment can serve also as a gene control apparatus or as a muscle related disorder therapeutic apparatus.

Second Embodiment

Figure 2:
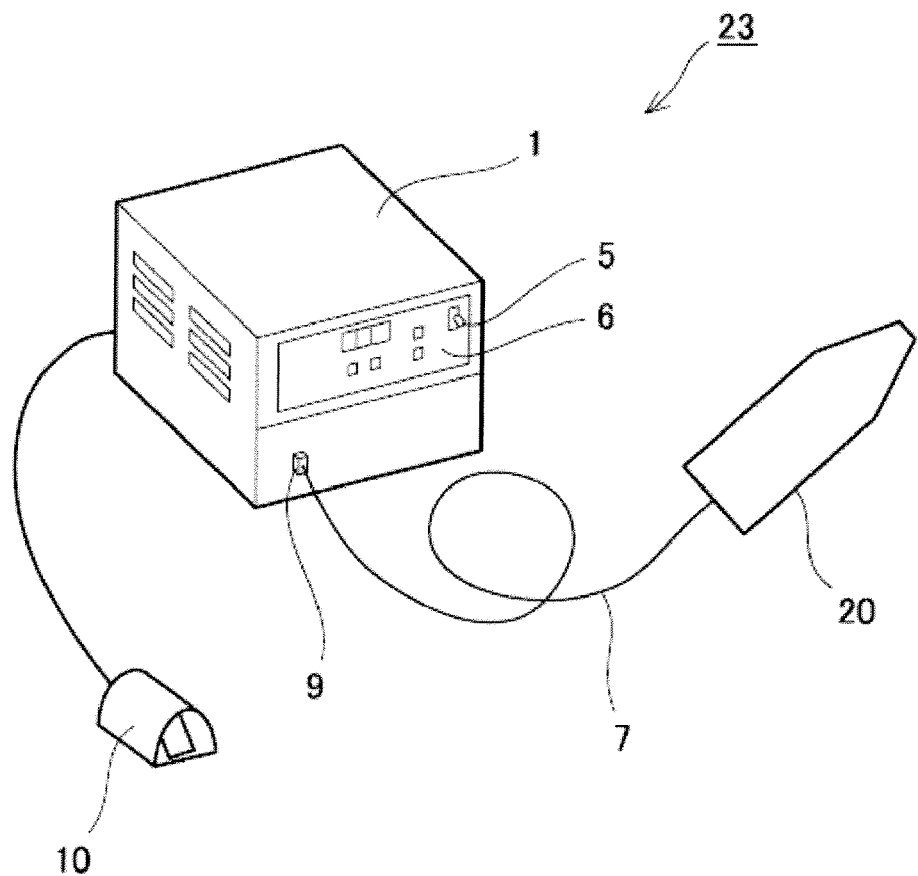
FIG. 2 is a schematic diagram showing an external view of a biostimulation apparatus according to a second embodiment of the present invention.

FIG. 2 is a schematic diagram showing an external view of a biostimulation apparatus according to a second embodiment of the present invention. A biostimulation apparatus 23 of the present invention is composed of a main unit 1, an irradiation gun 20 which is connected by a laser guide 7 of optical fiber to the main unit 1, and a foot switch 10 which is connected by a connecting cord to the main unit 1. The laser guide 7 is connected via an optical connector 9 to the main unit 1. Mounted on a side of the main unit 1 are an electric power supply key switch 5 and a console panel 6.

Figure 3:
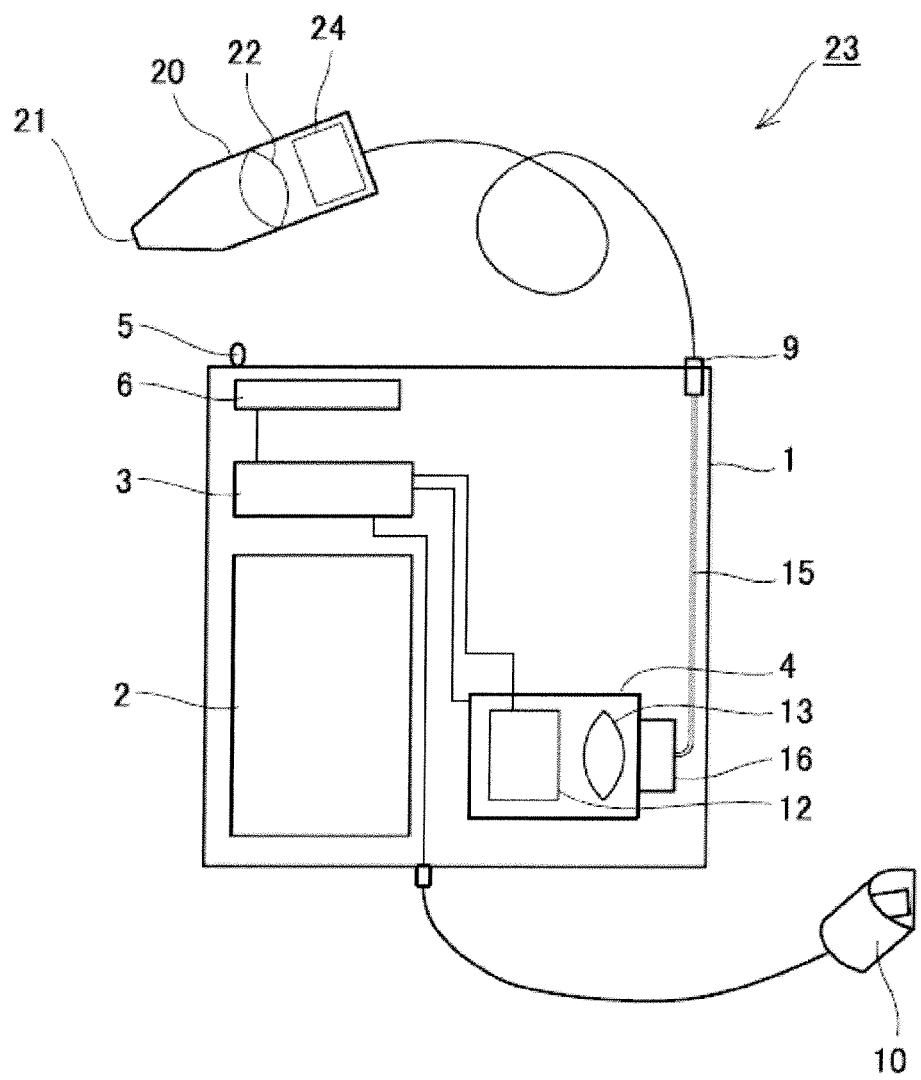
FIG. 3 is a schematic diagram showing a schematic configuration of the biostimulation apparatus shown in FIG. 2.

FIG. 3 is a schematic diagram showing a schematic configuration of the biostimulation apparatus 23 shown in FIG. 2. The main unit 1 of the biostimulation apparatus 23 houses therein an electric power supply part 2, a control part 3, and a laser part 4. The laser part 4 contains a laser oscillator 12 and a beam focusing lens 13. Connected to the laser part 4 is a pulse expander 16. A laser guide 15 of optical fiber is connected, at one end thereof, to the pulse expander 16 and at the other end thereof to the optical connector 9 mounted on a side of the main unit 1. The pulse expander 16 is to expand the pulse duration of the ultra short pulsed laser beam whereby interaction with the optical fiber is suppressed to effectively transmit laser beam. Laser beam oscillated by the laser oscillator 12 is converged by the beam focusing lens 13, expanded by the pulse expander 16, and then guided to the laser guide 15.

The control part 3 detects a signal from the console panel 6 and controls the laser part 4. The control part 3 further detects the on/off of the foot switch 10 and controls the output of the laser oscillator 12. Furthermore, the control part 3 controls the position of an objective lens 22 within the irradiation gun 20. The electric power supply part 2 supplies electric power to the control part 3, the console panel 6, the laser oscillator 12, the pulse expander 16, and the foot switch 10.

The irradiation gun 20 houses, in addition to the objective lens 22 by which laser beam is gathered, a pulse compressor 24 for compressing the pulse duration of laser beam from the laser guide 7. The leading end of the irradiation gun 20 constitutes a laser beam output end 21. The operator holds the laser beam output end 21 in such a manner that the laser beam output end 21 is brought into contact with the body of a subject, whereby laser beam is focused and a target portion of the body of the subject is irradiated with the laser beam.

A description will now be given of how to use the biostimulation apparatus 23 configured as described above. After turning on the power by the electric power supply key switch 5, the operator operates the console panel 6 to set the intensity, the pulse duration, the wavelength, the pulse number, the irradiation depth, and other like condition of the laser beam. Then, the operator holds the irradiation gun 20 so that the laser beam output end 21 of the irradiation gun 20 is positioned at an exposed portion of the subject of closest approach to the target portion. The control part 3 so controls the position of the objective lens 22 within the irradiation gun 20 as to achieve a preset irradiation depth. In response to an operation of the foot switch 10 by the operator, the control part 3 controls the laser part 4 so that laser beam is oscillated at a preset intensity, preset pulse duration, preset wavelength, and preset pulse number. The laser beam thus oscillated is gathered by the beam focusing lens 13, guided through the pulse expander 16 to the laser guide 15, guided via the optical connector 9 to the laser guide 7, and supplied through the pulse compressor 24 and then through the objective lens 22 within the irradiation gun 20 to the target portion from the laser beam output end 21.

The biostimulation apparatus 23 of the second embodiment can serve also as a gene control apparatus or as a muscle related disorder therapeutic apparatus.

In addition, the biostimulation apparatus of each of the first and second embodiments may be so configured as to further include an acupuncture point detector for discovering and deciding the position of an acupuncture point wherein, based on the information from the acupuncture point detector, the control part decides an irradiation portion. The acupuncture point detector may be configured such that, for example, skin resistance is measured and, based on the measured resistance value, the position of an acupuncture point is decided. Alternatively, the acupuncture point detector may be so configured as to include a distance meter wherein a distance from a specific point is measured using the distance meter and the result thereof is compared with the information on the position of acupuncture points prestored in the control part to decide the position of an acupuncture point.

In addition, in either the gene control apparatus or the muscle related disorder therapeutic apparatus having the same configuration as the biostimulation apparatus of each of the first and second embodiments, it may be arranged to further include a muscle measuring means for measuring the position and the mass of a muscle tissue. In such a configuration, it is possible, when the irradiation target is a muscle tissue, to accurately apply irradiation to the muscle tissue, whereby it becomes possible to determine a condition for irradiation depending on the muscle mass of a respective subject.

In addition, the biostimulation apparatus of each of the first and second embodiments can be used also for the improvement in blood flow as well as for the promotion of health.

Furthermore, it is also possible to apply an apparatus having the same configuration as the biostimulation apparatus of the second embodiment to a method of preventing a reduction, for example, in the leg muscle mass, or to a method of achieving an improvement in the leg blood flow, in a microgravity outer space in the inside of an orbiting space station or an interplanetary cruise spacecraft. In this case, it is possible to employ a configuration that further includes a fixture for fixing a part or all of the body of a living subject.

EXAMPLES

Experiment 1

The following experiments were conducted in order to confirm the effect of the irradiation of a living subject with femtosecond laser beam.

Figure 4:
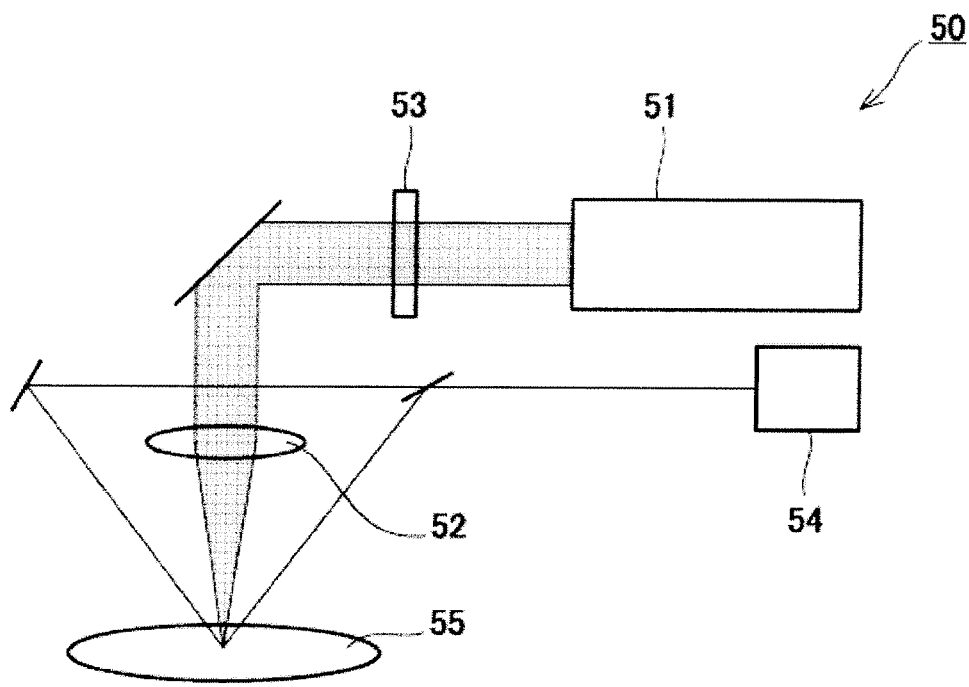
FIG. 4 is a schematic diagram showing a configuration of an experimental apparatus in Experiment 1 of a practical example.

FIG. 4 is a schematic diagram depicting a configuration of an experimental apparatus used in the present experiment. In an experimental apparatus 50, a high power femtosecond titanium-sapphire laser (Spectra-Physics: Hurricane) provided with a regenerative amplifier was used as the laser oscillator 51. Laser beam from the laser oscillator 51 was converged by a single lens 52 (f=150) and then emitted to both of the low legs of an inbred C57BL/6J mouse under Nembutal anesthesia. With respect to the laser beam, the wavelength was set at 800 nm, the pulse duration was set at 150 fs (full width at half maximum), and the pulse repetition frequency was set at 1 kHz. The laser-beam irradiation time was regulated by a mechanical shutter 53. In addition, the single-shot irradiation with laser beam was carried out in which the laser-beam oscillation frequency was set at 20 Hz and the gate time of the mechanical shutter 53 was set at 50 ms. In the figure, reference numeral 55 represents an irradiation target. Here, the irradiation position of the femtosecond laser beam was determined by a laser beam from an irradiation-guide laser oscillator 54 which is a helium-neon laser having a focal point at the same position as the laser oscillator 51.

The conditions for irradiation to one point of each specimen were as follows:

Specimen 1: 20 µJ/pulse, 1 kHz, 1 sec., energy total amount: 20 mW;

Specimen 2: 10 µJ/pulse, 1 kHz, 1 sec., energy total amount: 10 mW;

Specimen 3: 300 µJ/pulse, 1 shot, energy total amount: 0.3 mW

Under these conditions, a region of about 5 by 5 mm square of each specimen is irradiated at intervals of 500 µm. Consequently, the number of irradiation points is about 100. Like each of the specimens 1-3, a positive control (C) and a negative control (NC) which are laser-beam unirradiated control groups, too, are subjected to the following experiments.

After laser beam was emitted for 3 to 5 hours, skins and skeletal muscles (gastrocnemius and soleus muscles) in the laser irradiated portions were removed and the side of the right legs was subjected to gene expression analysis while on the other hand the side of the left legs was formalin-fixed and subjected to histochemical analysis.

Additionally, the extractive purification of total mRNA by TRIZOL and the synthesis of the cDNA by SuperScript RT (Gibco/BRL SuperScript Preamplification System) for the purpose of gene expression analysis, and paraffin embedding and HE stain for the purpose of histochemical analysis were conducted in a conventional manner. In the analysis for myostatin gene expression, a cDNA synthesized from a total RNA of about 2 µg by SuperScript RT (Gibco/BRL SuperScript Preamplification System, Gaithersburg, Md.), a primer of sense: 5'-GACAAAACACGAGGTACTCC-3' (SEQ ID NO: 1), and a primer of antisence: 5'-GATTCAGCCCATCT-TCTCC-3' (SEQ ID NO: 2) were used and amplification was conducted by Thermal Cycler (GeneAmp PCR System 9700; Applied Biosystems) in the following conditions: 26 to 27 cycles of 94 degrees Centigrade, 58 degrees Centigrade, and 72 degrees Centigrade. Next, after the agarose gel electrophoresis of PCR products, amplified gene bands were photographed and the value of integral was found by NIH Image (Wayne Rasband, National Institute of Health). In addition, by the use of a primer of sense: 5'-CATCTCACAGGTTACT-TCAGA-3' (SEQ ID NO: 3) and a primer of antisense: 5'-CT-GTTGCTGTAGCCGTATTC-3 (SEQ ID NO: 4), the G3PDH of an endogenous control was amplified by Thermal Cycler (GeneAmp PCR System 9700; Applied Biosystems) in the following conditions: 25 to 26 cycles of 94 degrees Centigrade, 58 degrees Centigrade, and 72 degrees Centigrade.

Figure 5:
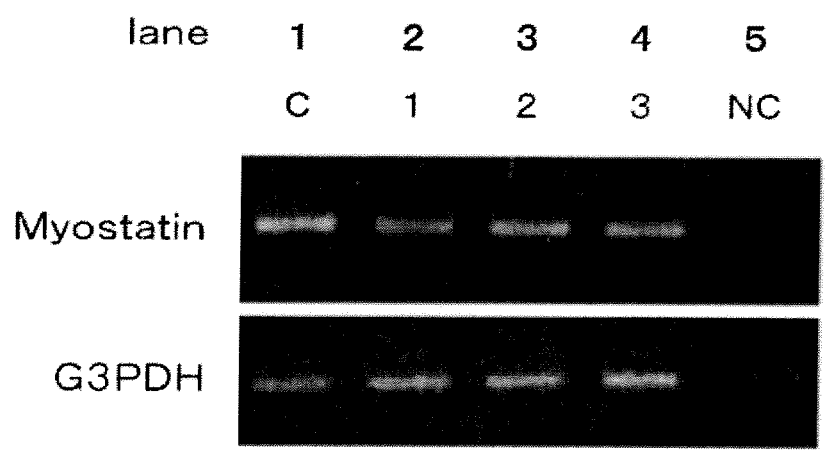
FIG. 5 is a diagram showing a photograph of an agarose gel after electrophoresis in Experiment 1.
Figure 6:
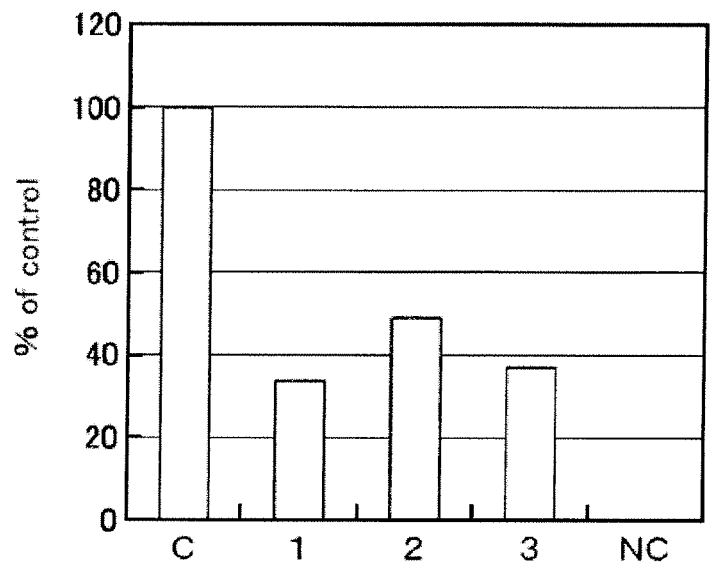
FIG. 6 is a diagram which shows an integral value, corrected using endogenous control, of the band of each specimen relating to the myostatin gene in the agarose gel of FIG. 5 and in which the result of a control group is taken as being 100%.

Next, after the agarose gel electrophoresis of PCR products, amplified gene bands were photographed and the value of integral was found by NIH Image (Wayne Rasband, National Institute of Health). Using this value as a basis, the band intensity of an amplified myostatin gene was corrected. FIG. 5 is a photograph of a post-electrophoresis agarose gel. Lane 1 shows the band of a positive control (C). Lanes 2-4 show the bands of Specimens 1-3, respectively. Lane 5 shows the band of a negative control (NC). FIG. 6 is a diagram representing the band intensity (after correction) of each lane of the myostatin gene, in which the result of the positive control (C) is taken as being 100%.

Figure 7:
FIG. 7 is a diagram showing, with respect to control group (a), specimen 1 (b), and specimen 3 (c), photographed images of formalin-fixed skeletal muscle tissues on the left leg side.
Figure 7:
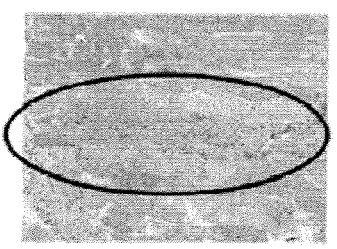
Figure 7:
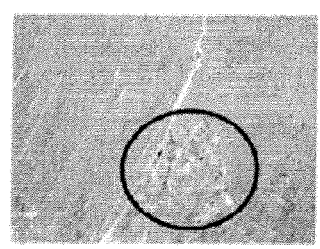

FIG. 7 is a diagram showing photographed images of skeletal muscle tissues on the left leg side which were fixed in formalin after laser irradiation. FIG. 7(a) is a tissue image of the control group (positive control). FIG. 7(b) is a tissue image of Specimen 1. FIG. 7(c) is a tissue image of Specimen 3. Parts enclosed by black circles are where laser beam was emitted.

As the result of the analysis, it was found that the expression of the myostatin gene is inhibited by the irradiation with femtosecond laser beam (see the results shown in FIGS. 5 and 6). In addition, the myostatin gene is a gene that is related to the restoration and regeneration of muscle tissues, and it has been known that the myostatin gene imbalance will lead to the hypertrophy of muscle tissues (see Mark Thomas et al., Myostatin, a Negative Regulator of Muscle Growth, Functions by Inhibiting Myoblast Proliferation; J. Biol. Chem., Vol. 275, Issue 51, 40235-40243, Dec. 22, 2000). It is conceivable that the myostatin gene expression is controlled by the irradiation with the ultra short pulsed laser beam, as in the present invention, for the acceleration of the growth of muscle cells. In addition, it was found that, unlike the irradiation of Specimen 1 with the laser beam for one second (the femtosecond laser beam was iteratively emitted about 1000 times), the one-shot irradiation of Specimen 3 with the femtosecond laser beam did not cause necrosis of skeletal muscle tissues. To sum up, on the one hand, it is observed that, in the one-second irradiation, the myostatin gene expression is inhibited, but the coagulation necrosis of tissues occurs. On the other hand, for the case of the one-shot irradiation with the femtosecond laser beam, the myostatin gene expression can be inhibited at the same level as the one-second irradiation and, besides, no coagulation necrosis is caused. Therefore, it can be said that the one-shot irradiation with the femtosecond laser beam is more preferable.

Experiment 2

The effect of electro-acupuncture stimulation on the myostatin gene expression was analyzed. The experiment used twenty mice. The mice were stimulated by electro-acupuncture stimulation for a given length of time. Thereafter, the myostatin gene expression analysis was conducted. In the electro-acupuncture stimulation, a needle of stainless steel (length: 40 mm; diameter: 0.16 mm; Seirin Kasei Co., Ltd., Shizuoka City) was inserted to a depth of 5 mm. Then, pulse stimulation of 1.2 Hz (output 2521-mV: from −1021 to +1500 mV) was applied for 15 minutes with the aid of a low-frequency energization stimulation apparatus (Kyushu Ryodoraku Ltd., Fukuoka City), and stimulated gastrocnemial and soleus muscles were removed for analysis. The following were prepared, namely a non-stimulated positive control (C), Specimens 4-7 after electro-acupuncture stimulation for 0, 1, 3, and 24 hours, respectively, and a negative control (NC).

After the PCR amplification and separation by agarose electrophoresis as in the above, the band of each gene was detected. In this case, the band intensity of an amplified myostatin gene was compared by the result corrected using the band intensity of the G3PDH of an endogenous control.

Figure 8:
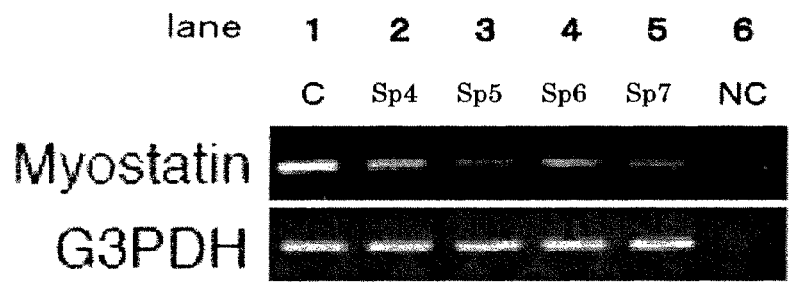
FIG. 8 is a diagram showing a photograph of an agarose gel after electrophoresis in Experiment 2.
Figure 9:
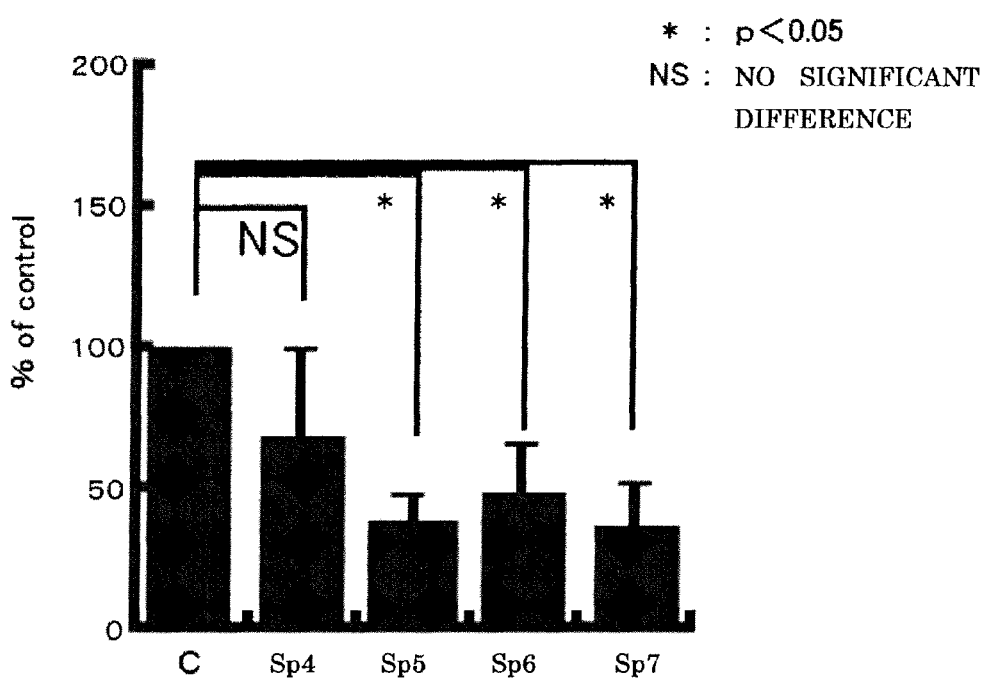
FIG. 9 is a diagram which shows an integral value of the band of each specimen relating to the myostatin gene in the agarose gel of FIG. 8 and in which the result of a control group (specimen 6) is taken as being 100%.

FIG. 8 is a photograph showing an agarose gel after electrophoresis. Lane 1 shows the result of the control (C). Lanes 2-5 show the results of the Specimens 4-7, respectively. Lane 6 shows the result of the negative control (NC). FIG. 9 is a diagram representing the band intensity of each band of the myostatin gene, in which the result of the positive control (C) is taken as being 100%.

As the result of the analysis, it was discovered that the myostatin gene expression is inhibited significantly ($P<0.05$) by electro-puncture stimulation (see the results shown in FIGS. 8 and 9).

The results of Experiment 1 and Experiment 2 show that, with respect to the action to the myostatin gene expression, the biostimulation method implemented by the present invention achieves the same effects as the electro-puncture stimulation. Therefore, the biostimulation method implemented by the present invention is useful also for preventing and treating a muscle related disorder known as an indication for acupuncture therapy, such as shoulder stiffness, frozen shoulder (stiff shoulder due to age), rheumatoid arthritis, myofascitis, neck muscle rigidity, neck-shoulder-arm syndrome, whiplash syndrome, sprain, tendon sheath inflammation, low back pain syndrome, skeletal muscle atrophy and the like.

It can be expected that the biostimulation method implemented by the present invention offers more benefits than mechanical stimulation by the insertion of an acupuncture needle. More specifically, for example, laser beam is able to stimulate a living tissue in a noncontact manner, thereby reducing the risk of infection and, in the second place, fast multi-point stimulation can be carried out by controlling the focal point of laser beam. Besides, it is considered that stimulation conditions can be optimized and standardized more easily than the acupuncture by controlling parameters such as the intensity of laser beam, the focal position of laser beam and other like parameter. In addition, the nonthermal stimulation of a living tissue by means of ultra short pulsed laser beam can be expected to serve as a therapeutic means superior to the acupuncture treatment performed by a skilled specialist.

INDUSTRIAL APPLICABILITY

The biostimulation apparatus, the gene control apparatus, or the muscle related disorder therapeutic apparatus according to the present invention is useful for therapeutic treatments in the health and medical field as well as in the sports medical field and, besides, for therapeutic treatments in outer space, specifically for the therapeutic treatment of muscle related disorders.

SEQUENCE LISTING FREE TEXT

SEQ ID NO:1, <223>: primer
SEQ ID NO:2, <223>: primer
SEQ ID NO:3, <223>: primer
SEQ ID NO:4, <223>: primer

What is claimed is:

1. A biostimulation apparatus comprising a laser oscillator for oscillating an ultra short pulsed laser beam and an optical system for focusing the ultra short pulsed laser beam;

the ultra short pulsed laser beam being focused by said optical system at a target portion of a living subject to cause the target portion to be irradiated with the laser beam to stimulate an acupuncture point;

wherein the target portion is either the acupuncture point or its periphery;

wherein the acupuncture point is stimulated by physical impact caused by the irradiation with the ultra short pulsed laser beam;

and wherein a pulse duration of the ultra short pulsed laser beam is in a range from $1.0 \times 10^{-10}$ sec to $1.0 \times 10^{-15}$ sec and a transient light intensity of the ultra short pulsed laser beam is in a range from $5 \times 10^5$ W to $1 \times 10^{18}$ W.

2. The biostimulation apparatus as set forth in claim 1, wherein continuity of a living tissue is not discontinued due to the irradiation with the ultra short pulsed laser beam.

3. The biostimulation apparatus as set forth in claim 1, wherein the ultra short pulsed laser beam is focused, in the target portion of the living subject, at a tissue under a surface of the living subject.

4. The biostimulation apparatus as set forth in claim 3, wherein the ultra short pulsed laser beam is focused, in the target portion of the living subject, at a depth in a range from 100 μm to 1 cm from the surface of the living subject.

5. The biostimulation apparatus as set forth in claim 1, wherein a wavelength of the ultra short pulsed laser beam is in a range from 600 to 1200 nm.

6. The biostimulation apparatus as set forth in claim 1, wherein the target portion is situated either in a skin tissue or in a muscle tissue.

7. The biostimulation apparatus as set forth in claim 1 further comprising acupuncture point detection means for detecting an acupuncture point and control means for deciding the target portion based on information from the acupuncture point detection means.

8. The biostimulation apparatus as set forth in claim 1, wherein improvement in blood flow is accelerated by stimulating the acupuncture point.

9. A gene control apparatus comprising a laser oscillator for oscillating an ultra short pulsed laser beam and an optical system for focusing the ultra short pulsed laser beam;

wherein the ultra short pulsed laser beam is focused by said optical system at a target portion of a living subject to cause the target portion to be irradiated with the laser beam to control an expression level of a particular gene;

wherein the expression level of the particular gene is controlled using physical impact caused by the irradiation with the ultra short pulsed laser beam;

and wherein a pulse duration of the ultra short pulsed laser beam is in a range from $1.0 \times 10^{-10}$ sec to $1.0 \times 10^{15}$ sec and a transient light intensity of the ultra short pulsed laser beam is in a range from $5 \times 10^5$ W to $1 \times 10^{18}$ W.

10. The gene control apparatus as set forth in claim 9, wherein continuity of a living tissue is not discontinued due to the irradiation with the ultra short pulsed laser beam.

11. The gene control apparatus as set forth in claim 9, wherein the ultra short pulsed laser beam is focused, in the target portion of the living subject, at a tissue under a surface of the living subject.

12. The gene control apparatus as set forth in claim 11, wherein the ultra short pulsed laser beam is focused, in the target portion of the living subject, at a depth in a range from 100 μm to 1 cm from the surface of the living subject.

13. The gene control apparatus as set forth in claim 9, wherein a wavelength of the ultra short pulsed laser beam is in a range from 600 to 1200 nm.

14. The gene control apparatus as set forth in claim 9, wherein the ultra short pulsed laser beam is focused, by the optical system, at a target portion in a muscle tissue of the living subject to cause the target portion to be irradiated with the laser beam to control the expression level of a myostatin gene in the muscle tissue.

15. The gene control apparatus as set forth in claim 14, wherein enforcement or restoration of the muscle tissue or both are accelerated by controlling the expression level of the myostatin gene.

16. A muscle related disorder therapeutic apparatus comprising a laser oscillator for oscillating an ultra short pulsed laser beam and an optical system for focusing the ultra short pulsed laser beam;

wherein the ultra short pulsed laser beam is focused, by the optical system, at a target portion in a muscle tissue of a living subject to cause the target portion to be irradiated with the laser beam to treat a muscle related disorder;

wherein the muscle related disorder is treated using physical impact caused by the irradiation with the ultra short pulsed laser beam;

and wherein a pulse duration of the ultra short pulsed laser beam is in a range from $1.0 \times 10^{-10}$ sec to $1.0 \times 10^{-15}$ sec and a transient light intensity of the ultra short pulsed laser beam is in a range from $5 \times 10^5$ W to $1 \times 10^{18}$ W.

17. The muscle related disorder therapeutic apparatus as set forth in claim 16, wherein continuity of a living tissue is not discontinued due to the irradiation with the ultra short pulsed laser beam.

18. The muscle related disorder therapeutic apparatus as set forth in claim 16, wherein the ultra short pulsed laser beam is focused, in the target portion of the living subject, at a tissue under a surface of the living subject.

19. The muscle related disorder therapeutic apparatus as set forth in claim 18, wherein the ultra short pulsed laser beam is focused, in the target portion of the living subject, at a depth in a range from 100 μm to 1 cm from the surface of the living subject.

20. The muscle related disorder therapeutic apparatus as set forth in claim 16, wherein a wavelength of the ultra short pulsed laser beam is in a range from 600 to 1200 nm.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gacaaaacac gaggtactcc                                                   20

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
gattcagccc atcttctcc                                                    19

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
catctcacag gttacttcag a                                                 21

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ctgttgctgt agccgtattc                                                   20